US008649259B2

(12) United States Patent
Allan et al.

(10) Patent No.: US 8,649,259 B2
(45) Date of Patent: Feb. 11, 2014

(54) METHOD AND APPARATUS FOR IMPLEMENTING CONTROL OF MULTIPLE PHYSICALLY DUAL HOMED DEVICES

(75) Inventors: David Allan, Ottawa (CA); Peter Ashwood-Smith, Hull (CA)

(73) Assignee: Rockstar Consortium US LP, Plano, TX (US)

( * ) Notice: Subject to any disclaimer, the term of this patent is extended or adjusted under 35 U.S.C. 154(b) by 0 days.

(21) Appl. No.: 13/471,712

(22) Filed: May 15, 2012

(65) Prior Publication Data
US 2012/0230183 A1 Sep. 13, 2012

Related U.S. Application Data

(63) Continuation of application No. 12/487,407, filed on Jun. 18, 2009, now Pat. No. 8,184,648.

(51) Int. Cl.
*G01R 31/08* (2006.01)

(52) U.S. Cl.
USPC ........... 370/218; 370/219; 370/256; 370/351; 370/401; 709/238

(58) Field of Classification Search
USPC ........... 370/218, 219, 256, 351, 401; 709/238
See application file for complete search history.

(56) References Cited

U.S. PATENT DOCUMENTS

| | | | |
|---|---|---|---|
| 5,299,312 A | 3/1994 | Rocco | |
| 5,489,896 A * | 2/1996 | Sofer et al. | 370/445 |
| 5,953,314 A | 9/1999 | Ganmukhi et al. | |
| 6,188,689 B1 * | 2/2001 | Katsube et al. | 370/389 |
| 6,195,351 B1 * | 2/2001 | Hiscock et al. | 370/389 |
| 6,246,692 B1 | 6/2001 | Dai et al. | |
| 6,594,776 B1 * | 7/2003 | Karighattam et al. | 714/4.12 |
| 7,093,027 B1 * | 8/2006 | Shabtay et al. | 709/239 |
| 7,246,168 B1 * | 7/2007 | Bales | 709/228 |
| 7,345,991 B1 * | 3/2008 | Shabtay et al. | 370/221 |
| 7,386,876 B2 * | 6/2008 | Kim | 726/3 |
| 7,403,523 B2 * | 7/2008 | Nguyen et al. | 370/390 |
| 7,411,963 B2 | 8/2008 | Ward et al. | |
| 7,639,605 B2 | 12/2009 | Narayanan et al. | |
| 7,643,468 B1 * | 1/2010 | Arregoces et al. | 370/351 |
| 7,751,416 B2 * | 7/2010 | Smith et al. | 370/410 |

(Continued)

OTHER PUBLICATIONS

International Search Report for PCT/CA2010/00935 mailed Oct. 12, 2010, 10 pages.

(Continued)

*Primary Examiner* — Andrew Lai
*Assistant Examiner* — Andrew C Lee
(74) *Attorney, Agent, or Firm* — Withrow & Terranova, PLLC

(57) ABSTRACT

A ring control protocol is used to establish a separate control plane for a plurality of physically dual homed devices to enable collections of dual homed devices to be represented by a single pair of addresses into the attached routed Ethernet network. The gateway devices analyze the passing ring control packets to create direct mappings for data packets to the routed Ethernet network. Thus, although the dual homed devices are treated as a ring from a control perspective, the data path is implemented to be direct so that data packets continue to flow directly from the dual homed devices to each of the attached gateway devices. In one embodiment, each of the gateway devices implements a virtual switch and advertises the MAC address of the virtual switch into the routed Ethernet network rather than the MAC addresses of each of the attached Ethernet Switch Units.

18 Claims, 4 Drawing Sheets

(56) References Cited

U.S. PATENT DOCUMENTS

| | | | |
|---|---|---|---|
| 7,782,763 B2* | 8/2010 | Balus et al. | 370/218 |
| 7,925,817 B2 | 4/2011 | Uehara et al. | |
| 7,974,388 B2* | 7/2011 | Sadot | 379/45 |
| 8,018,841 B2 | 9/2011 | Holness et al. | |
| 8,077,709 B2* | 12/2011 | Cai et al. | 370/389 |
| 8,125,928 B2* | 2/2012 | Mehta et al. | 370/254 |
| 8,284,656 B2* | 10/2012 | Saha et al. | 370/219 |
| 8,467,316 B1* | 6/2013 | Goli et al. | 370/256 |
| 2002/0010869 A1* | 1/2002 | Kim | 713/201 |
| 2002/0019958 A1 | 2/2002 | Cantwell et al. | |
| 2002/0023170 A1 | 2/2002 | Seaman et al. | |
| 2002/0191250 A1 | 12/2002 | Graves et al. | |
| 2003/0185149 A1 | 10/2003 | Daniell et al. | |
| 2003/0189898 A1* | 10/2003 | Frick et al. | 370/227 |
| 2004/0100970 A1* | 5/2004 | Gerdisch et al. | 370/395.53 |
| 2005/0066216 A1* | 3/2005 | Hebbar et al. | 714/1 |
| 2005/0190752 A1* | 9/2005 | Chiou et al. | 370/360 |
| 2005/0276215 A1 | 12/2005 | Kitani et al. | |
| 2007/0047436 A1* | 3/2007 | Arai et al. | 370/219 |
| 2007/0076719 A1 | 4/2007 | Allan et al. | |
| 2007/0165648 A1* | 7/2007 | Joo | 370/395.54 |
| 2008/0159124 A1* | 7/2008 | Sasaki | 370/217 |
| 2008/0183854 A1* | 7/2008 | Hopen et al. | 709/223 |
| 2008/0225695 A1 | 9/2008 | Balus et al. | |
| 2008/0239946 A1 | 10/2008 | Morita | |
| 2008/0279096 A1* | 11/2008 | Sullivan et al. | 370/221 |
| 2008/0304477 A1* | 12/2008 | Froroth et al. | 370/360 |
| 2009/0168647 A1* | 7/2009 | Holness et al. | 370/228 |
| 2009/0168671 A1* | 7/2009 | Holness et al. | 370/256 |
| 2009/0276842 A1* | 11/2009 | Yevmenkin et al. | 726/13 |
| 2010/0020680 A1* | 1/2010 | Salam et al. | 370/225 |
| 2010/0142544 A1 | 6/2010 | Chapel et al. | |
| 2010/0189117 A1* | 7/2010 | Gowda et al. | 370/401 |
| 2010/0284413 A1* | 11/2010 | Abdullah et al. | 370/401 |

OTHER PUBLICATIONS

Notice of Allowance for U.S. Appl. No. 12/487,407 mailed Jan. 25, 2012, 9 pages.

Final Office Action for U.S. Appl. No. 12/487,407 mailed Oct. 25, 2011, 16 pages.

Non-final Office Action for U.S. Appl. No. 12/487,407 mailed Apr. 26, 2011, 10 pages.

Preliminary Report on Patentability for PCT/CA2010/00935 mailed Jun. 18, 2009, 5 pages.

* cited by examiner

METHOD AND APPARATUS FOR IMPLEMENTING CONTROL OF MULTIPLE PHYSICALLY DUAL HOMED DEVICES

RELATED APPLICATION

This application is a continuation of co-pending U.S. patent application Ser. No. 12/487,407, filed on Jun. 18, 2009, entitled METHOD AND APPARATUS FOR IMPLEMENTING CONTROL OF MULTIPLE PHYSICALLY DUAL HOMED DEVICES, which is hereby incorporated herein by reference in its entirety.

TECHNICAL FIELD

The present invention relates to communication networks and, more particularly, to a method and apparatus for implementing control of multiple physically dual homed devices.

BACKGROUND

Data communication networks may include various switches, routers, hubs, and other devices coupled to and configured to receive data and forward the data on the network. These devices will be referred to herein as "network elements." A network element is generally not a consumer of the data, but rather is used to receive and forward data so that the data may pass through the network. Data is communicated through a network by enabling the network elements to pass protocol data units, such as frames, packets, cells or segments, between each other over communication links. A particular protocol data unit may be handled by multiple network elements and cross multiple communication links as it travels between its source and its destination over the network.

The various network elements on the communication network communicate with each other using predefined sets of rules, referred to herein as protocols. Different protocols are used to govern different aspects of the communication, such as how signals should be formed for transmission between the network elements, various aspects of what the protocol data units should look like, how protocol data units should be handled or routed through the network by the network elements, and how information such as routing information should be exchanged between the network elements.

A network service provider will generally implement one or more data centers to enable customers to connect to a communication network such as the Internet. Likewise, in an enterprise, a data center may be used to house servers that enable users to connect to the corporate network or which provide other services on the network. Example services include database services, email services, etc.

In a data center, a large number of servers (e.g. 24 servers) may be housed in a rack and connected to an Ethernet Switch Unit which connects the servers to a communication network. Typically, the Ethernet Switch Unit will be co-located with the rack of servers. The Ethernet switch unit will then connect to a large Gateway switch which will connect the Ethernet switch unit to higher bandwidth network such as a routed Ethernet network.

FIG. 1 shows an example data center in which servers 10 connect to one or more Ethernet switch units 12, which in turn are connected to gateways 14. The gateways 14 provide connectivity to a routed Ethernet network 16. The Ethernet switch units will generally be dual-homed to a pair of gateway switches so that, if one of the gateway switches should fail, the other gateway can assume responsibility for forwarding traffic into the routed Ethernet network. For example, in FIG. 1, each of the Ethernet switch units 12 are connected to two different gateways (e.g. dual homed) to a pair of gateway switches 14. The gateway switches may individually assume responsibility to represent particular ESUs into the routed Ethernet network or, alternatively, may collaboratively represent the ESUs into the routed Ethernet network by treating the links from the ESUs to the gateways as a split multi-link trunk.

Although it is possible to envision multiple ESUs in a chain connected to a pair of gateway nodes, such a configuration is vulnerable to multiple failures. Hence dual homing of individual switches directly to the gateways is desirable since the configuration is less susceptible to failure.

Large data centers may require layer two connectivity for communities of 10s to 100s of thousands of servers. To enable this configuration to be able to scale, one of the key metrics to consider is the number of MAC addresses the gateway is required to advertise into the routed Ethernet network to represent the set of subtending servers. Specifically, when the ESU is connected directly to the gateway, the gateway will need to advertise the MAC address of the port via which the ESU is reached into the routed Ethernet network Normally as the number of Ethernet switch units increases, the associated number of ports, and hence the number of MAC addresses being advertised into the routed Ethernet network (e.g. an Ethernet network implemented using 802.1aq Shortest Path Backbone Bridging, although this may also apply to 802.1ah spanning tree controlled Ethernet networks) may become excessive and expensive for the core to maintain. Accordingly, it would be advantageous to provide a way to reduce the number of MAC addresses that is required to be advertised into the routed Ethernet network.

SUMMARY OF THE INVENTION

One or more ring control protocol instances are run on the multiple physically dual homed devices in such a way that enables collections of dual homed devices to be represented by a single pair of addresses into the attached routed Ethernet network. The gateway devices analyze the passing ring control packets to create direct mappings for data packets to the routed Ethernet network. Thus, although the dual homed devices are treated as a ring from a control perspective, the data path is implemented to be direct so that data packets continue to flow directly from the dual homed devices to each of the attached gateway devices. Each of the gateway devices implements one or more virtual switches, which each serve to aggregate traffic from multiple attached ESUs into the routed Ethernet network. Each virtual switch advertises its own MAC address into the routed Ethernet network rather than the MAC addresses of each of the attached Ethernet Switch Units so that fewer MAC addresses will be advertised by each of the gateways. When resiliency is provided for by a peer gateway, frames may be send to and received from the ESU directly or via the peer gateway (in failure scenarios). Frames that are received from the Ethernet switch units are encapsulated at the virtual switch using a new Ethernet header identifying the virtual switch as the source of the data packets. In the reverse direction, frames of data will be addressed to the virtual switch, which will demux packets using the C-MAC Ethernet header to pass the frames onto the correct output port to the correct Ethernet switch unit. By running a separate control plane between the Ethernet switch units and the gateway, a set of Ethernet switch units is able to be represented into the routed Ethernet network using a pair of MAC addresses, while enabling data paths to continue to flow directly between the Ethernet switch units and the routed Ethernet network.

BRIEF DESCRIPTION OF THE DRAWINGS

Aspects of the present invention are pointed out with particularity in the appended claims. The present invention is illustrated by way of example in the following drawings in which like references indicate similar elements. The following drawings disclose various embodiments of the present invention for purposes of illustration only and are not intended to limit the scope of the invention. For purposes of clarity, not every component may be labeled in every figure. In the figures:

DETAILED DESCRIPTION

Figure 1:
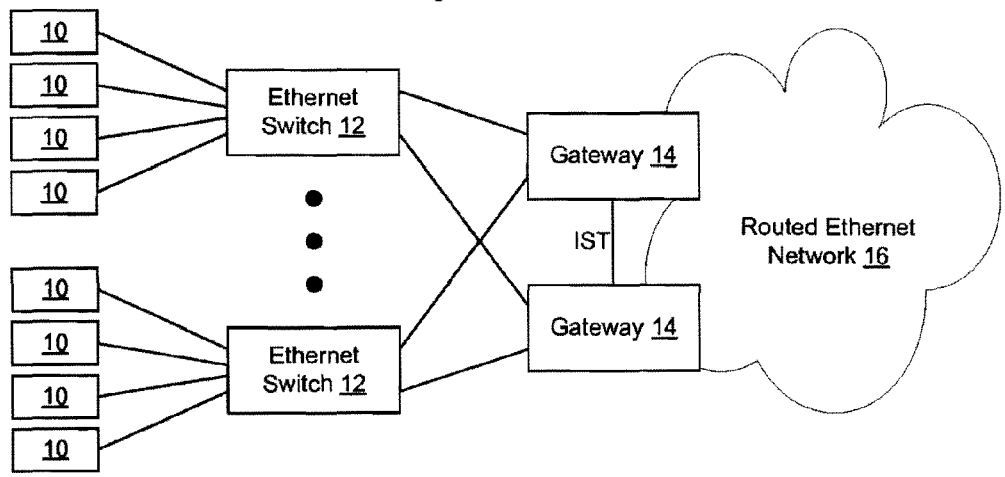
FIG. 1 is a functional diagram of a reference network showing a dual homed connection between Ethernet Switch Units and a pair of gateways.
Figure 2:
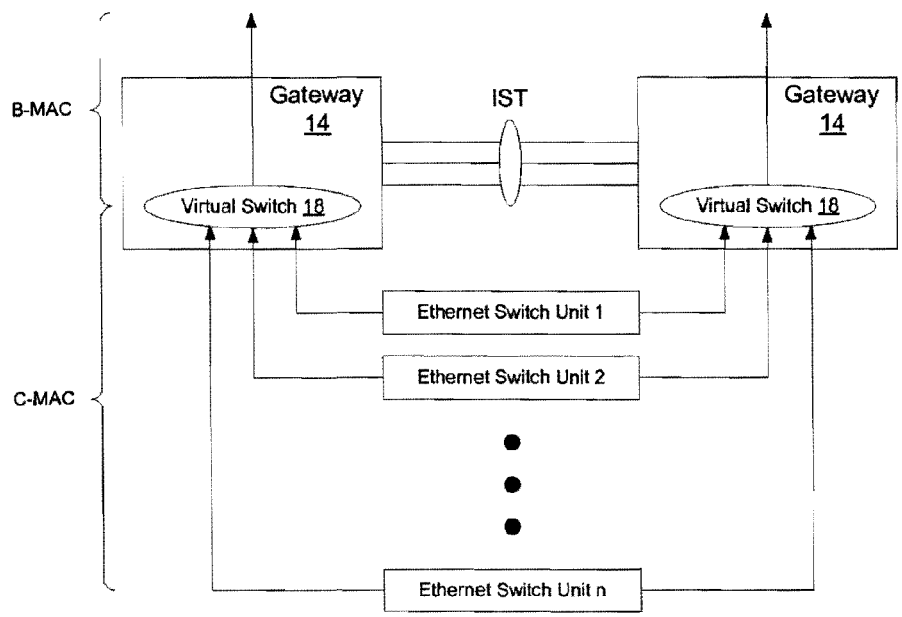
FIG. 2 is a functional block diagram showing physical dual homed Ethernet switch units interconnecting with a pair of gateway switches.

FIG. 2 is a functional block diagram showing physical dual homed Ethernet switch units interconnecting with a pair of gateway switches. As shown in FIG. 2, each of the Ethernet switch units connects via one or more links to two or more Gateways 14. According to an embodiment, each of the gateways implements at least one virtual switch 18 that summarizes traffic from a plurality of Ethernet switch units into the routed Ethernet network 16. In one embodiment, the virtual switch performs Mac-in-Mac encapsulation to add a B-MAC Ethernet header to the traffic as described in IEEE 802.1ah. Each gateway may implement multiple virtual switches, each of which is responsible for handling traffic for a set of the attached Ethernet switch units. By implementing a virtual switch, sets of subtending ESUs that have a common peer gateway may be represented by a single MAC address into the routed Ethernet network rather than requiring each ESU to be individually represented into the routed Ethernet network. Hence, the number of MAC addresses advertised into the core network may be reduced to increase scalability of the network.

According to an embodiment of the invention, one or more instances of a separate control plane is implemented between the virtual switches and attached set of physically dual homed devices (e.g. Ethernet switch units). The control plane, in one embodiment, is implemented using a ring control protocol so that control messages, e.g. link state advertisements, will follow the logical ring rather than following the data path on the network. By utilizing a ring control protocol, control messages may be exchanged between the set of attached physical devices while enabling the set of attached physical devices to be represented into the attached routed Ethernet network using a pair of MAC addresses. However, whereas the control plane is implemented using a ring architecture, the data path from each physically dual homed device to the associated gateways remains point-to-point so that the selection of a ring-based control protocol does not affect the data traffic patterns on the network.

It should be noted that simply having a common MAC address for all devices connected to the gateway node in many cases is not sufficient, this is because under failure of the node the recovery actions may not be aligned. There may be customers directly attached to the switch, or sets of switches for which there is a different peer gateway in the dual homed arrangement. Hence a MAC address is assigned for a set of subtending switches that have a common recovery behavior under failure.

Ethernet Shared Protection Rings (E-SPRING) is a protocol designed to be used to control an Ethernet ring network having a group of serially interconnected nodes. E-SPRING is defined as ITU-T SG15/Q9, G.8032, which specifies how the nodes on the ring should handle unicast, multicast, and broadcast frames. It also specifies multiple service classes, failure handling, and other aspects of how traffic should be forwarded by nodes on the Ethernet ring. The manner in which an Ethernet ring operates is also described in greater detail in U.S. patent application Ser. No. 12/027,942, entitled Method And Apparatus For Controlling A Set Of Ethernet Nodes Interconnected To Form One Or More Closed Loops, filed Feb. 7, 2008, the content of which is hereby incorporated herein by reference. In one embodiment, the control plane associated with the interconnection between the gateways and Ethernet switch units is implemented using a ring control protocol. U.S. patent application Ser. No. 12/344,355, filed Dec. 26, 2008, describes a way of enabling a network implemented using a ring control protocol to be dual homed into an Ethernet network implementing a spanning tree control protocol, and U.S. patent application Ser. No. 12/344,362, filed Dec. 26, 2008, describes a way of enabling a ring network implemented using a ring control protocol to be dual homed into an Ethernet network implementing traffic engineered trunks. The content of each of these applications is hereby incorporated herein by reference.

Figure 3:
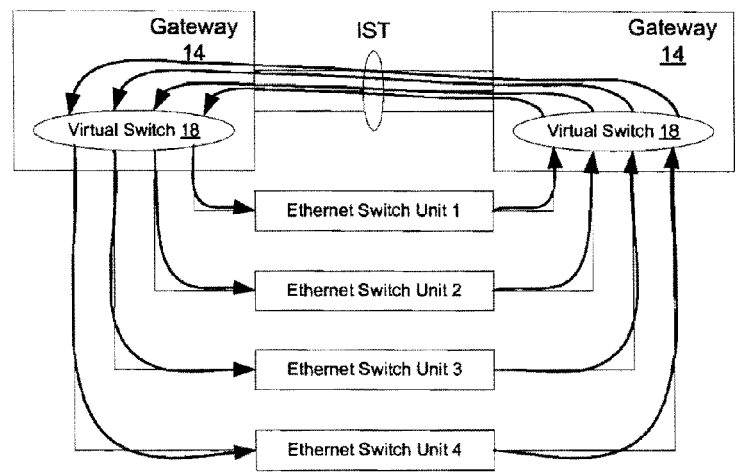
FIG. 3 shows the flow of control information between the network devices arranged as shown in FIG. 2 according to one embodiment of the invention.
Figure 4:
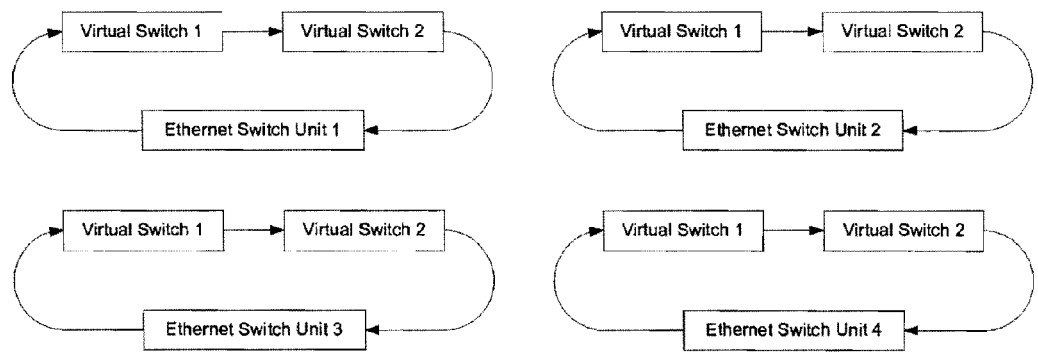
FIG. 4 shows the logical flow of control information in the embodiment of FIG. 3.

FIG. 3 shows one example of how a ring control protocol may be used according to one embodiment of the invention. In this embodiment, each gateway has implemented a virtual switch that summarizes routes from the multiple Ethernet switch units into a single BMAC for advertisement on the network. In this example, a separate ring protocol instance is used for each Ethernet Switch Unit. For example, as shown in FIG. 4, a separate ring control instance may be used to create a logical control ring including one of the virtual switch instances in each of the gateways, as well as one of the Ethernet switch units. Thus, in FIG. 4, a first ring control protocol instance is used to control Ethernet switch 1 and includes Ethernet Switch Unit 1, virtual switch 1, and virtual switch 2. Likewise, a second ring control protocol instance is used to control Ethernet switch 2. In this embodiment, the second ring control protocol instance includes Ethernet switch 2, virtual switch 1, and virtual switch 2.

The ring control protocol enables traffic to be forwarded from the Ethernet switch unit to the correct gateway in a persistent manner so that link failures between the Ethernet switch units and the gateways is transparent to the routed network. For example, assume that traffic from Ethernet switch unit 1 was to be forwarded by the left gateway in FIG. 2 onto the routed Ethernet network. The ring control protocol may implement a blocking port on the port leading to the right gateway, so that traffic flows from the Ethernet switch unit to the left gateway. If there is a failure on the link between Ethernet Switch Unit 1 and the left gateway, the ring control protocol will automatically remove the blocking port and move the blocking port to be adjacent the failure. This will cause the Ethernet switch unit to forward traffic out toward the gateway on the right. The virtual switch in the right gateway will know that it is not responsible for forwarding traffic into the routed Ethernet network and will forward the traffic along the ring over the IST to the left gateway. The virtual switch in the left gateway will thus receive the traffic from the Ethernet switch unit 1 via the IST and forward the traffic into the routed Ethernet network. By implementing a ring control protocol, local failures between the Ethernet switch units and the gateway may be hidden from the routed Ethernet network, so that each end of the ring appears as an invariant B-MAC.

Figure 8:
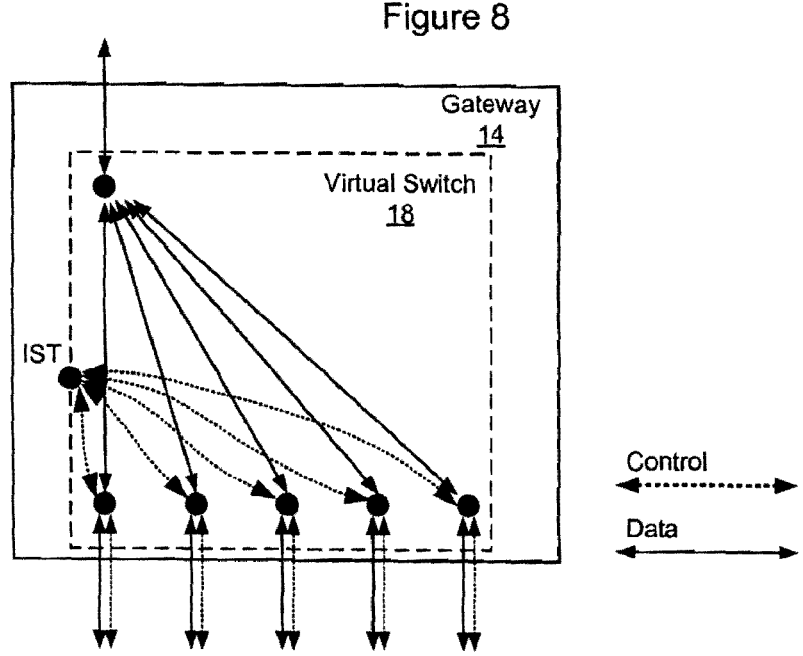
FIG. 8 shows the flow of data and the flow of control information through one of the gateways according to the embodiment of the invention shown in FIGS. 3-4.

Although the control traffic flows as shown in FIG. 3, the data traffic from each of the switch units is passed to the selected virtual switch and is passed from the virtual switch onto the attached routed Ethernet network. FIG. 8 shows an example of how the control traffic and data traffic would be handled by a virtual switch. As shown in FIG. 8, the virtual switch will forward data traffic onto the routed Ethernet network and will forward control traffic over the IST to enable the control traffic to pass over the ring to the other virtual switch. Of course, as described above, under failure conditions there may be instances where the virtual switch will also forward data traffic over the IST. Accordingly, each virtual switch will only forward traffic for that set of ESUs that it is responsible to represent into the routed Ethernet network.

Figure 5:
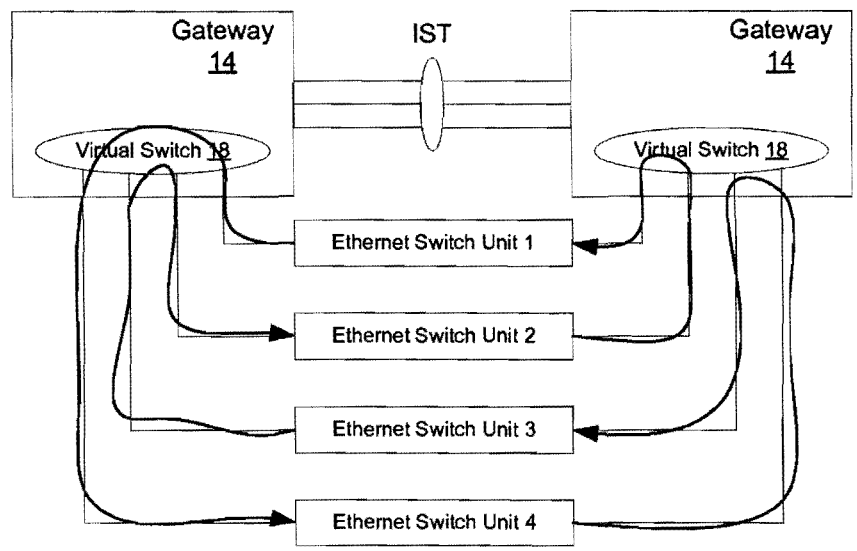
FIGS. 5-6 show the flow of control information between the network devices arranged as shown in FIG. 2 according to another embodiment of the invention.
Figure 6:
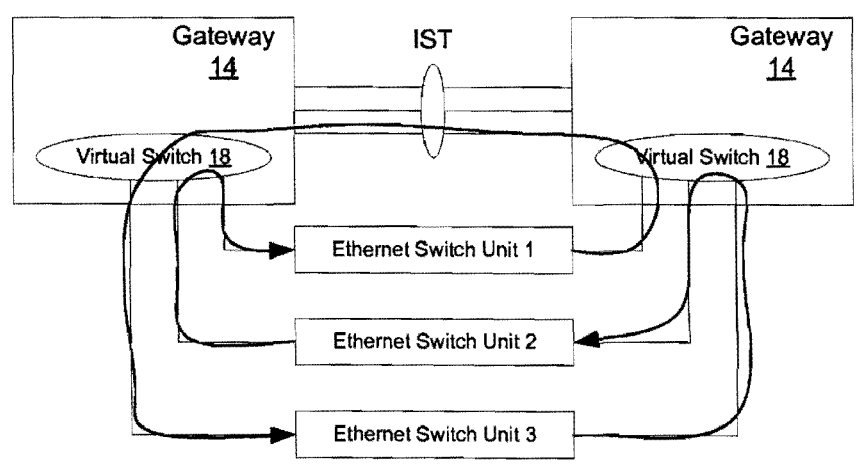
Figure 7:
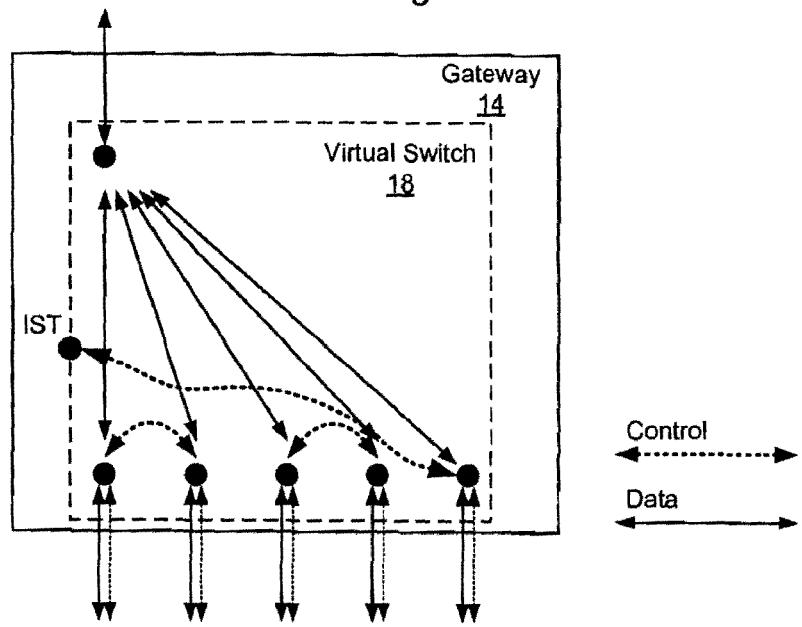
FIG. 7 shows the flow of data and the flow of control information through one of the gateways according to the embodiment of the invention shown in FIGS. 5-6.

FIGS. 5-7 show another embodiment where groups of Ethernet switch units are logically formed into a single ring for control purposes by causing the gateway switches to u-turn control packets to enable multiple Ethernet switch units to exist on a common control ring. In the embodiment shown in FIG. 5, there are an even number of Ethernet switch units, which enables each of the gateway switches to directly interconnect each of the Ethernet switch units on the ring. FIG. 6 shows another example in which there is an odd number of Ethernet switch units. In this instance one of the branches of the logical ring will need to extend over the Inter-switch trunk to complete the ring. Although the example shown in FIG. 6 has the control traffic being passed over the IST, the invention is not limited in this regard as the control traffic could instead be passed by the virtual switch over the attached routed network.

FIG. 7 shows the difference between the data path and the control path in a gateway node. As shown in FIG. 7, interconnecting the Ethernet switch units in a logical ring for control purposes only affects the flow of control packets between the Ethernet switch units. Specifically, in the embodiment shown in FIG. 7 the control packets are looped back to enable a group of Ethernet switch units to be logically interconnected in a ring (e.g. as shown in FIG. 5 or 6) so that a ring control protocol may be used to manage these devices. However, the data path associated with the Ethernet switch units is still point to point so that, when the gateway receives a data packet, it will forward the data packets directly onto the PLSB network in a normal manner. Thus, implementing the control plane using a ring control protocol does not affect the manner in which the gateway switches handle data traffic on the network or how the gateway switches forward data onto the PLSB network.

The virtual switch 18 performs MAC learning to learn MAC addresses reachable via the attached ESU by watching the unique port the ESU is attached to. When the gateway receives a data packet from an attached Ethernet switch unit, it will pass the packet to the virtual switch, which will perform BMAC encapsulation to enable the packet to be forwarded over the attached routed Ethernet network. In the reverse direction, when the gateway receives a packet from the routed Ethernet network, the virtual switch will read the client MAC address and use the mapping to select an output port to forward the packet to the correct Ethernet switch unit.

As discussed above, each of the Ethernet Switch Units aggregates traffic from multiple clients. Traffic from that ESU may then be forwarded to a particular gateway or, alternatively, may be forwarded to virtual switches on two or more gateways. Likewise, traffic from a particular ESU may be forwarded to two or more virtual switches implemented on the same gateway. Traffic from a particular ESU may be transmitted in one or more VLANs to enable traffic to be directed to different virtual switches within the same ESU, so that each ESU can aggregate a portion of the traffic for the ESU into the attached routed Ethernet network.

The functions described above may be implemented as a set of program instructions that are stored in a computer readable memory and executed on one or more processors on the computer platform. However, it will be apparent to a skilled artisan that all logic described herein can be embodied using discrete components, integrated circuitry such as an Application Specific Integrated Circuit (ASIC), programmable logic used in conjunction with a programmable logic device such as a Field Programmable Gate Array (FPGA) or microprocessor, a state machine, or any other device including any combination thereof. Programmable logic can be fixed temporarily or permanently in a tangible medium such as a read-only memory chip, a computer memory, a disk, or other storage medium. All such embodiments are intended to fall within the scope of the present invention.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense.

What is claimed is:

1. A method of coupling at least one Ethernet switch unit comprising an Ethernet switch unit Media Access Control (MAC) address to a routing-protocol-controlled Ethernet network, the method comprising:

dual homing the at least one Ethernet switch unit on a pair of gateways connected to the routing-protocol-controlled Ethernet network, the pair of gateways being connected by an inter-gateway trunk;

configuring the at least one Ethernet switch unit and the pair of gateways to implement a control plane logical ring linking the at least one Ethernet switch unit to the pair of gateways;

associating a common Media Access Control (MAC) address of the routing-protocol-controlled Ethernet network with each Ethernet switch unit linked to the pair of gateways via the control plane logical ring; and representing, into the routing-protocol-controlled Ethernet network at one of the gateways using the common MAC address in lieu of the Ethernet switch unit MAC address, packets received from each Ethernet switch unit linked to the pair of gateways via the control plane logical ring.

2. The method of claim 1, comprising coupling a plurality of Ethernet switch units to the routing-protocol-controlled Ethernet network by:

dual homing each Ethernet switch unit on the pair of gateways;
configuring the plurality of Ethernet switch units and the pair of gateways to implement a separate control plane logical ring for each Ethernet switch unit;
associating a respective MAC address of the routing-protocol-controlled Ethernet network with each Ethernet switch unit; and
representing, into the routing-protocol-controlled Ethernet network at one of the gateways using the respective MAC address of the routing-protocol-controlled Ethernet network, each Ethernet switch unit linked to the pair of gateways via the separate control plane logical ring.

3. The method of claim 2, wherein representing, into the routing-protocol-controlled Ethernet network at one of the gateways using the respective MAC address, each Ethernet switch unit linked to the pair of gateways via the separate control plane logical ring comprises representing some of the Ethernet switch units at one gateway and representing others of the Ethernet switch units at the other gateway.

4. The method of claim 1, comprising coupling a plurality of Ethernet switch units to the routing-protocol-controlled Ethernet network by:
dual homing each Ethernet switch unit of the plurality of Ethernet switch units on the pair of gateways, each Ethernet switch unit have a different Ethernet switch unit MAC address associated therewith;
configuring the plurality of Ethernet switch units and the pair of gateways to implement a common control plane logical ring for the plurality of Ethernet switch units;
associating the common MAC address of the routing-protocol-controlled Ethernet network with each Ethernet switch unit of the plurality of Ethernet switch units; and
representing, into the routing-protocol-controlled Ethernet network at one of the gateways using the common MAC address in lieu of the Ethernet switch unit MAC address associated with each Ethernet switch unit, packets received from each Ethernet switch unit linked to the pair of gateways via the common control plane logical ring.

5. The method of claim 4, wherein representing, into the routing-protocol-controlled Ethernet network at one of the gateways using the common MAC address, each Ethernet switch unit linked to the pair of gateways via the common control plane logical ring comprises representing some of the Ethernet switch units at one gateway and representing others of the Ethernet switch units at the other gateway.

6. The method of claim 1, comprising coupling a plurality of Ethernet switch units to the routing-protocol-controlled Ethernet network by:
dual homing each Ethernet switch unit on the pair of gateways;
configuring the plurality of Ethernet switch units and the pair of gateways to implement plural control plane logical rings, each control plane logical ring linking at least one Ethernet switch unit to the pair of gateways;
associating a respective common MAC address of the routing-protocol-controlled Ethernet network with the Ethernet switch units of each control plane logical ring; and
representing, into the routing-protocol-controlled Ethernet network at one of the gateways using the respective common MAC address, each Ethernet switch unit linked to the pair of gateways via the control plane logical ring.

7. The method of claim 6, comprising grouping together, into each separate control plane logical ring, Ethernet switch units requiring common recovery behavior under failure.

8. The method of claim 6, wherein representing, into the routing-protocol-controlled Ethernet network at one of the gateways using the respective common MAC address, each Ethernet switch unit linked to the pair of gateways via the control plane logical ring comprises representing some of the Ethernet switch units at one gateway and representing others of the Ethernet switch units at the other gateway.

9. The method of claim 1, wherein representing, into the routing-protocol-controlled Ethernet network at one of the gateways using the common MAC address, each Ethernet switch unit linked to the pair of gateways via the control plane logical ring comprises advertising the common MAC address into the routing-protocol-controlled Ethernet network such that data traffic can be directed over the routing-protocol-controlled Ethernet network to each Ethernet switch unit linked to the pair of gateways via the control plane logical ring using the common MAC address.

10. The method of claim 1, comprising configuring each Ethernet switch unit with a direct data path to the pair of gateways such that data traffic does not follow the control plane logical ring.

11. The method of claim 1, comprising operating the control plane logical ring according to the Ethernet shared protection rings (E-SPRING) protocol.

12. The method of claim 1, comprising configuring at least one virtual switch at each gateway to summarize routes from Ethernet switch units homed on the each gateway.

13. The method of claim 12, comprising configuring the at least one virtual switch to encapsulate data traffic passing into the routing-protocol-controlled Ethernet network from an Ethernet switch unit with the common MAC address of the routing-protocol-controlled Ethernet network which is associated with the Ethernet switch unit.

14. The method of claim 12, comprising configuring the at least one virtual switch to decapsulate data traffic passing from the routing-protocol-controller Ethernet network to an Ethernet switch unit to remove a routing-protocol-controlled Ethernet network MAC address.

15. The method of claim 1, wherein for each control plane logical ring linking an odd number of Ethernet switch units to the pair of gateways, the gateways use the inter-gateway trunk to complete the control plane logical ring.

16. The method of claim 1, comprising:
forwarding control plane traffic from a first Ethernet switch unit in the control plane logical ring to a first gateway of the pair of gateways;
forwarding the control plane traffic from the first gateway to a second Ethernet switch unit in the control plane logical ring; and
forwarding the control plane traffic from the second Ethernet switch unit to a second gateway of the pair of gateways.

17. The method of claim 16, further comprising forwarding the control plane traffic from the second gateway to the first gateway via the inter-gateway trunk.

18. The method of claim 16, further comprising forwarding the control plane traffic from the second gateway to a third Ethernet switch unit in the control plane logical ring.

* * * * *